United States Patent
Cheng et al.

(10) Patent No.: US 11,742,697 B1
(45) Date of Patent: Aug. 29, 2023

(54) INDUCTIVE MODULE AND DEVICE

(71) Applicant: National Yang Ming Chiao Tung University, Hsinchu (TW)

(72) Inventors: Yu-Ting Cheng, Hsinchu (TW); Jui-Yu Hsu, Hsinchu (TW); Chung-Yu Wu, Hsinchu (TW); Ming-Dou Ker, Zhubei (TW)

(73) Assignee: National Yang Ming Chiao Tung University, Hsinchu (TW)

( * ) Notice: Subject to any disclaimer, the term of this patent is extended or adjusted under 35 U.S.C. 154(b) by 0 days.

(21) Appl. No.: 17/884,927

(22) Filed: Aug. 10, 2022

(30) Foreign Application Priority Data

Feb. 22, 2022 (TW) .................................. 111106321

(51) Int. Cl.
*H02J 50/00* (2016.01)
*H01Q 15/00* (2006.01)
*H02J 50/10* (2016.01)
*A61N 1/378* (2006.01)

(52) U.S. Cl.
CPC ....... *H02J 50/005* (2020.01); *H01Q 15/0086* (2013.01); *H02J 50/10* (2016.02); *A61N 1/3787* (2013.01)

(58) Field of Classification Search
CPC .... H02J 50/005; H02J 50/10; H01Q 15/0086; A61N 1/3787
USPC ....................................................... 307/104
See application file for complete search history.

(56) References Cited

U.S. PATENT DOCUMENTS

| | | | | |
|---|---|---|---|---|
| 8,907,531 | B2 * | 12/2014 | Hall | H01F 27/34 323/911 |
| 10,692,643 | B2 * | 6/2020 | Ridler | H01F 38/14 |
| 10,978,902 | B2 | 4/2021 | Ker et al. | |
| 2013/0261700 | A1 * | 10/2013 | Lee | A61N 1/36046 607/53 |
| 2018/0221673 | A1 * | 8/2018 | Kuang | A61N 1/37229 |

FOREIGN PATENT DOCUMENTS

TW   I671972 B   9/2019

OTHER PUBLICATIONS

Conghui Lu et al., "A Dual-Band Negative Permeability and Near-Zero Permeability Metamaterials for Wireless Power Transfer System," IEEE Transactions on Industrial Electronics, 68(8), pp. 7072-7082, 2021.

(Continued)

*Primary Examiner* — Alfonso Perez Borroto
(74) *Attorney, Agent, or Firm* — Michael Best & Friedrich LLP

(57) ABSTRACT

An inductive module with a miniaturized metamaterial structure includes an insulating substrate, two coil units, and a magnetic unit. The insulating substrate has opposing first and second surfaces and a through hole extending between the first and second surfaces. The coil units are respectively disposed on the first surface and the second surface of the insulating substrate, and are electrically connected to each other through the through hole. Each of the coil units includes a closed loop coil. The magnetic unit corresponds in position to a portion of the coil unit, surrounds said portion of the coil unit, and has an opening.

16 Claims, 7 Drawing Sheets

(56) References Cited

OTHER PUBLICATIONS

Kuan-Jung Chen et al., "A 13.56 MHz Metamaterial for the Wireless Power Transmission Enhancement in Implantable Biomedical Devices," 2019 20th International Conference on Solid-State Sensors, Actuators and Microsystems & Eurosensors XXXIII (Transducers & Eurosensors XXXIII), pp. 1439-1442, 2019.
F. Bilotti et al., "Design of Spiral and Multiple Split-Ring Resonators for the Realization of Miniaturized Metamaterial Samples," IEEE Transactions on Antennas and Propagation, 55(8), pp. 2258-2267, 2007.
Bui Xuan Khuyen et al., "Size-efficient Metamaterial Absorber at Low Frequencies: Design, Fabrication, and Characterization," Journal of Applied Physics, 117(24), pp. 243105-1~243105-7, 2015.

* cited by examiner

INDUCTIVE MODULE AND DEVICE

CROSS-REFERENCE TO RELATED APPLICATION

This application claims priority of Taiwanese Invention Patent Application No. 111106321, filed on Feb. 22, 2022.

FIELD

The disclosure relates to an inductive module, and more particularly to an inductive module with a miniaturized metamaterial structure.

BACKGROUND

Metamaterial refers to a conductive material being processed to have a special structure that is capable of generating parasitic capacitance, inductance that converges electromagnetic waves, and an evanescent waves gain, i.e., to enhance the amplitude of the evanescent wave, and thus can be applied to coil wireless transmission and improve efficiency thereof.

In general, the size of the metamaterial used in products having an operating frequency of 13.56 MHz is usually relatively large, and therefore is deemed to be unsuitable for commercialization. Currently, one can increase the number of coil turns and the length of the coil in order to improve the inductance value, which in turn reduces the size of the metamaterial. However, due to internal resistance of the coil, such method will also increase electromagnetic loss and adversely affect the transmission efficiency.

SUMMARY

Therefore, an object of the disclosure is to provide an inductive module capable of alleviating at least one of the drawbacks of the prior art.

According to an aspect of the disclosure, an inductive module with a miniaturized metamaterial structure includes an insulating substrate, two coil units, and at least one magnetic unit. The insulating substrate has a first surface, a second surface opposite to the first surface, and a through hole extending between the first surface and the second surface. The coil units are respectively disposed on the first surface and the second surface of the insulating substrate, and are electrically connected to each other through the through hole. Each of the coil units includes at least one closed loop coil. The magnetic unit corresponds in position to a portion of at least one of the coil units, surrounds the portion of the at least one of the coil units, and has an opening.

According to another aspect of the disclosure, an inductive device includes a plurality of inductive modules. Each of inductive modules includes an insulating substrate, two coil units, and at least one magnetic unit. For each of the inductive modules, the insulating substrate has a first surface, a second surface opposite to the first surface, and a through hole extending between the first surface and the second surface. For each of the inductive modules, the coil units are respectively disposed on the first surface and the second surface of the insulating substrate, and are electrically connected to each other through the through hole. Each of the coil units includes at least one closed loop coil. For each of the inductive modules, the magnetic unit corresponds in position to a portion of at least one of the coil units, surrounds the portion of the at least one of the coil units, and has an opening. The inductive modules are arranged in an array and juxtaposed with one another

BRIEF DESCRIPTION OF THE DRAWINGS

Other features and advantages of the disclosure will become apparent in the following detailed description of the embodiment with reference to the accompanying drawings, of which.

DETAILED DESCRIPTION

Figure 1:
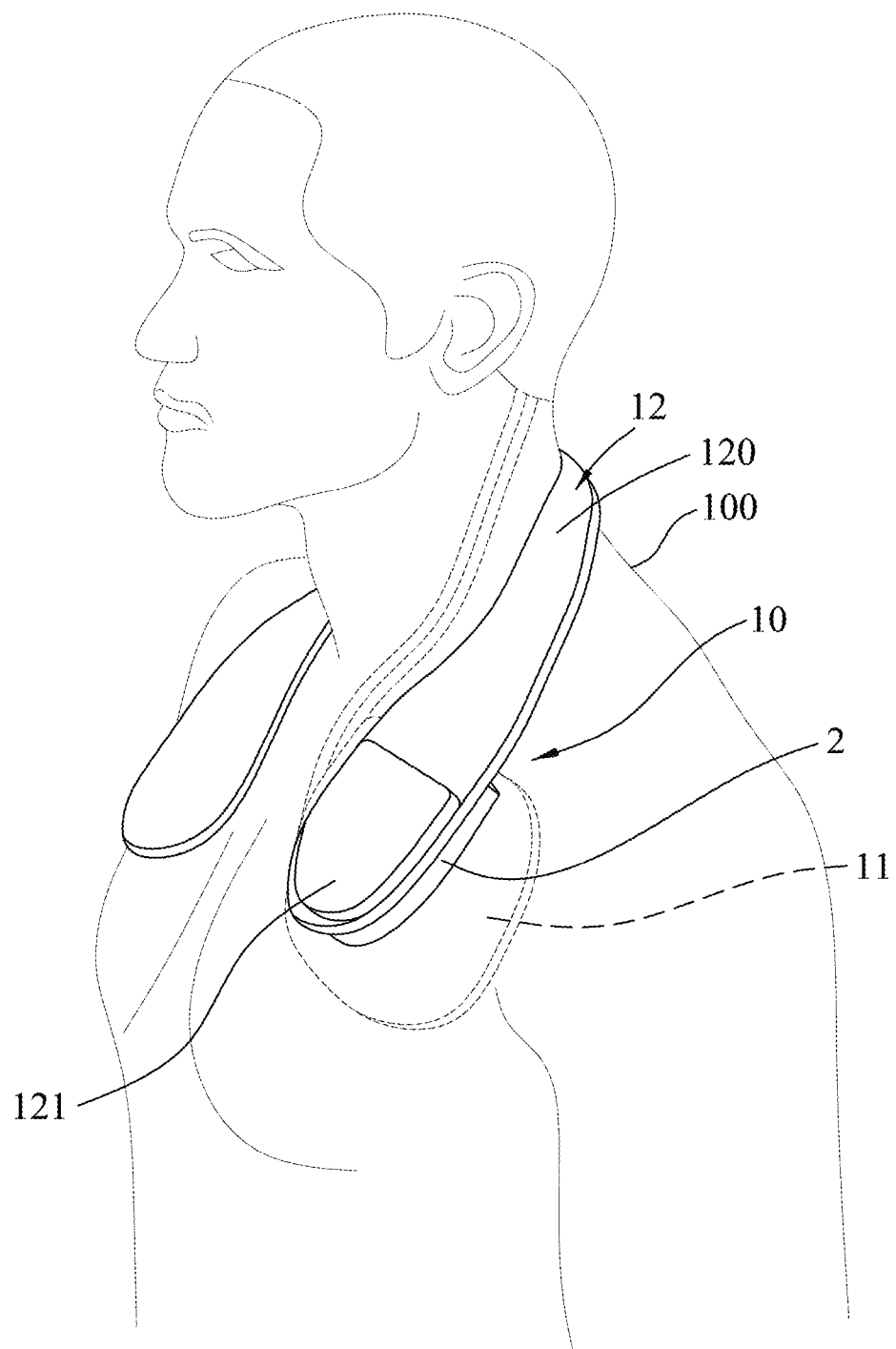
FIG. 1 is a schematic view of an inductive module of the present disclosure being applied to a wireless charging medical device worn on a user.

Before the disclosure is described in greater detail, it should be noted that where considered appropriate, reference numerals or terminal portions of reference numerals have been repeated among the figures to indicate corresponding or analogous elements, which may optionally have similar characteristics.

Figure 2:
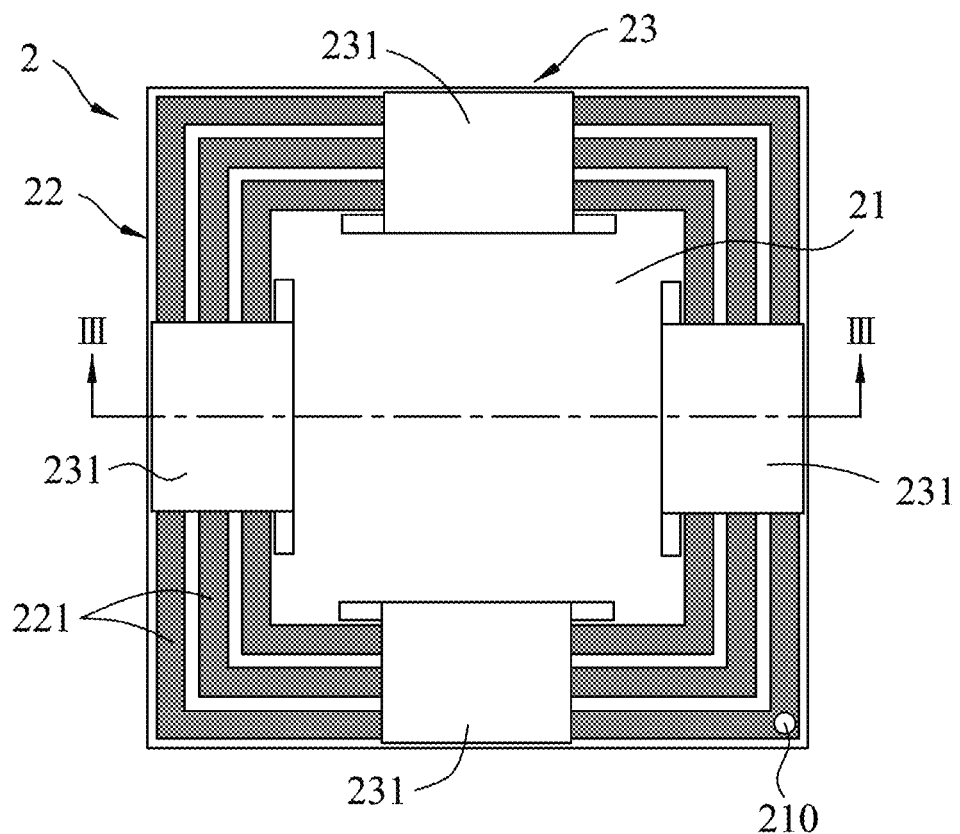
FIG. 2 is a schematic top view of an inductive module according to an embodiment of the present disclosure.
Figure 3:
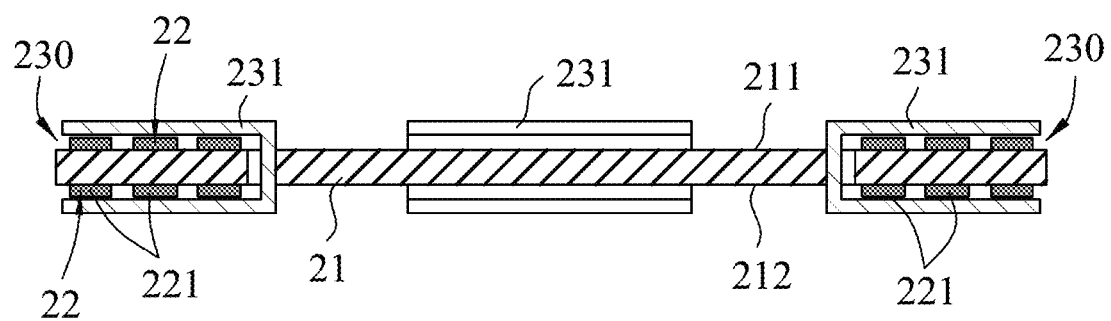
FIG. 3 is a schematic sectional view of the embodiment taken along line in FIG. 2.

FIGS. 1 to 3 illustrate an embodiment of an inductive module 2 with a miniaturized metamaterial structure according to the present disclosure adapted to be used in a wireless charging device worn on a user. The inductive module 2 is capable of generating a relatively large inductance value so as to increase efficiency of wireless power transmission. In this embodiment, the wireless charging device is exemplified as a wireless charging implantable medical device 10.

As shown in FIG. 1, the implantable medical device 10 includes a brain pacemaker 11 and a wireless charger 12. The brain pacemaker 11 is implanted into the body 100 of the user and is operable to stimulate a target portion of the brain of the user. The wireless charger 12 includes a main body 120 that is to be worn on the user, a charging module 121 that is mounted to the main body 120 at a position adjacent to the brain pacemaker 11 when being worn on the user and that is configured to wirelessly charge the brain pacemaker 11, and the inductive module 2 of the embodiment that is mounted to the main body 120 opposite to the charging module 121 and that is located between the brain pacemaker 11 and the wireless charger 12 when the wireless charger 12 is worn on the user.

As shown in FIGS. 2 and 3, the inductive module 2 includes an insulating substrate 21, two coil units 22, and a magnetic set 23 which has a plurality of magnetic units 231. The insulating substrate 21 has a first surface 211, a second surface 212 opposite to the first surface 211, and a through hole 210 extending between the first surface 211 and the second surface 212. In this embodiment, the insulating substrate 21 is a printed circuit board and is rectangular in shape but not limited to this example.

The coil units 22 are respectively disposed on the first surface 211 and the second surface 212 of the insulating substrate 21, and are electrically connected to each other through the through hole 210. Each of the coil units 2 includes a plurality of closed loop coils 221. In this embodiment, the coil units 22 are made of copper, and the closed loop coils 221 are formed concentrically and proximally to an outer peripheral edge of the insulating substrate 21. Specifically, for each of the coil units 22, at least three closed loop coils 221 are formed on the respective one of the first surface 211 and the second surface 212 and are radially spaced apart from one another. It should be noted that the number of the closed loop coils 221 and the configuration thereof are not limited to this example and can be modified according to a frequency band as required.

Each of the magnetic units 231 corresponds in position to a portion of each of the coil units 22, and surrounds the portion of each of the coil units 22 by extending from one of the coil units 22 to the other one of the coil units 22. The magnetic units 231 are arranged in pairs, and each pair of the magnetic units 231 are located respectively at two positions that are symmetrical with respect to a center of the close loop coils 221. Each of the magnetic units 231 has an opening 230, forms an open loop, and partially loops around a portion of each of the closed loop coils 221. In this embodiment, the magnetic units 231 are made of a soft magnetic material.

Specifically, the magnetic units 231 are angularly spaced apart from one another around the center of the closed loop coil 221. The quantity of the magnetic units 231 is of an even number. In this embodiment, the quantity of the magnetic units 231 is four, and the magnetic units 231 are disposed on four side edges of the insulating substrate 21 and are located at symmetrical positions to cover the coil units 22. The magnetic units 231 are arranged in pairs, and the openings 230 of each pair of the magnetic units 231 face away from each other and each of the magnetic units 231 is C-shaped.

Figure 4:
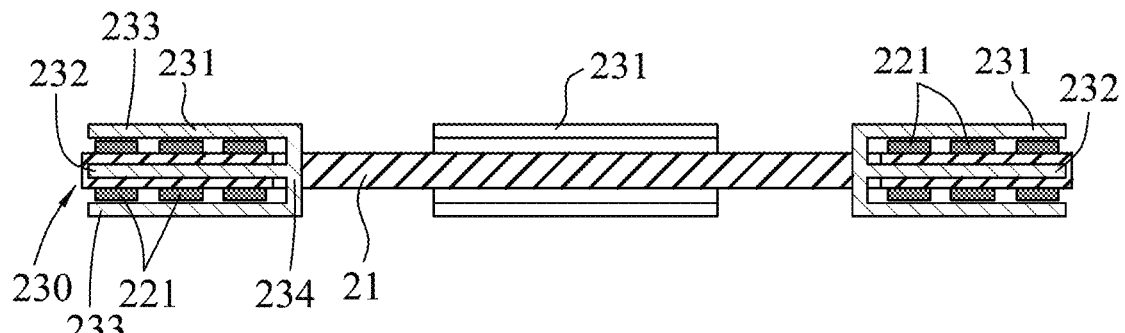
FIG. 4 is a schematic sectional view of a modification of the embodiment.
Figure 5:
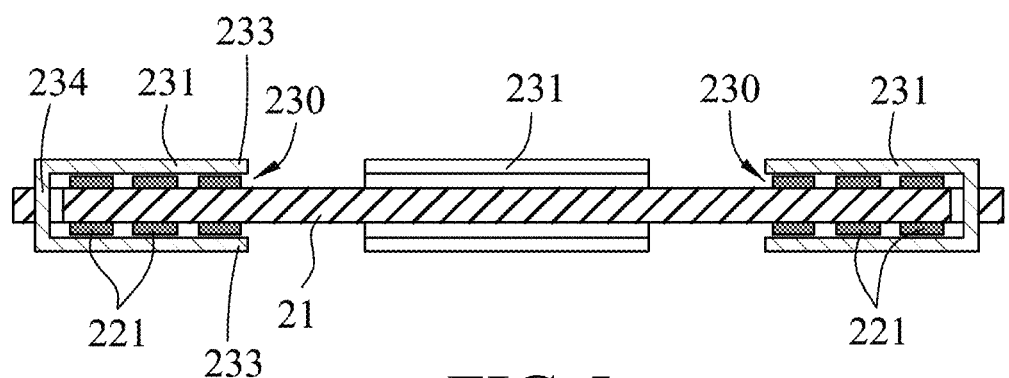
FIG. 5 is a schematic sectional view of another modification of the embodiment.
Figure 6:
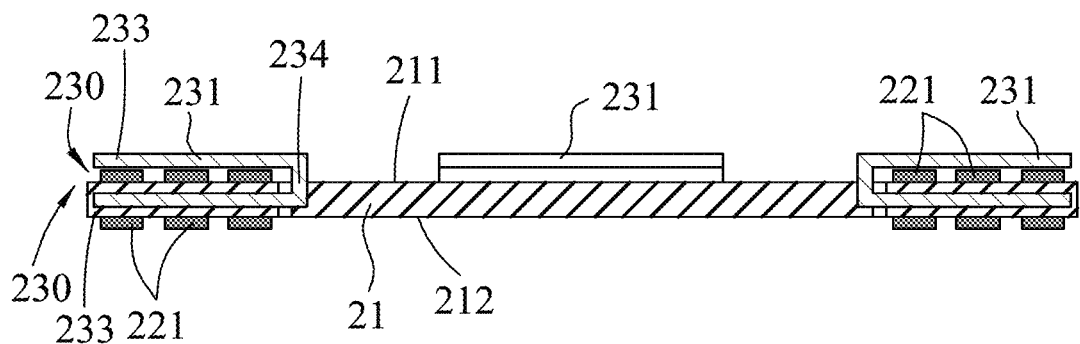
FIG. 6 is a schematic sectional view of yet another modification of the embodiment.

Referring to FIGS. 4 to 6, the magnetic units 231 may have different configurations and be modified as long as each of the magnetic units 231 partially covers a portion of each of the close loop coils 221 and has the opening 230. For example, as shown in FIG. 4, in a modification of the embodiment, each of the magnetic units 231 has two free ends 233 disposed at two opposing sides of the opening 230 and an insert portion 234 inserted in the insulating substrate 21 and facing the opening 230. The insert portion 234 of each of the magnetic units 231 has an intermediate projection 232 pointing towards the opening 230 such that each of the magnetic units 231 is E-shaped. In other words, the close loop coils 221 of the coil units 22 formed on the first surface 211 and the second surface 212 are located on opposite sides (i.e., upper and lower sides) of the intermediate projection 232 of each of the magnetic units 231. In another modification of the embodiment, as shown in FIG. 5, each of the magnetic units 231 is C-shaped, and the openings 230 of each pair of the magnetic units 231 face toward each other. That is to say, each of the openings 320 faces the center of the insulating substrate 21. As shown in FIG. 6, in yet another modification of the embodiment, the magnetic units 231 are similar to the magnetic units 231 shown in FIG. 3, and the difference therebetween resides in that one of the free ends 233 of each of the magnetic units 231 is inserted in the insulating substrate 21 such that the magnetic units 231 only cover a portion of the close loop coils 221 disposed on the first surface 211 of the insulating substrate 21.

By virtue of the structural design of the magnetic units 231 of the inductive module 2, the inductance value of the close loop coils 211 can be significantly increased without increasing the number of turns or the length of the close loop coils 221. Thus, it is advantageous to apply the inductive module of the present disclosure in implantable medical devices.

Figure 7:
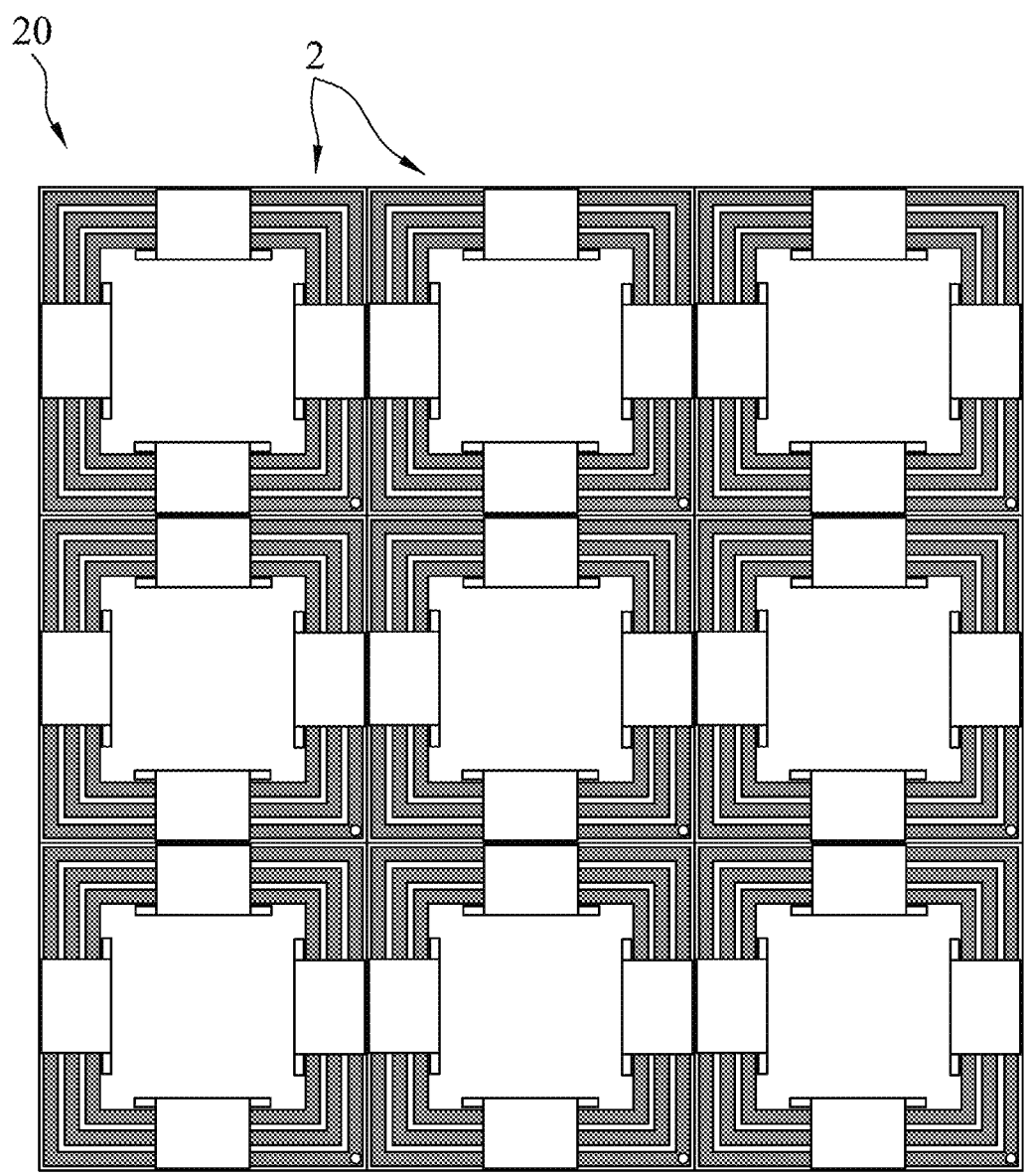
FIG. 7 is a schematic top view of an inductive device including a plurality of the inductive modules of the embodiment being arranged in an array.

Referring to FIG. 7, an inductive device 20 that includes a plurality of inductive modules 2 with a miniaturized metamaterial structure of the present disclosure is shown. The inductive modules 2 are arranged in a matrix array of n×m and are juxtaposed with one another, where n and m are positive integers and are greater than or equal to two. In this example, the inductive modules 2 are arranged in a 3×3 array, but arrangement of the inductive modules 2 of the present disclosure is not limited to this example.

Figure 8:
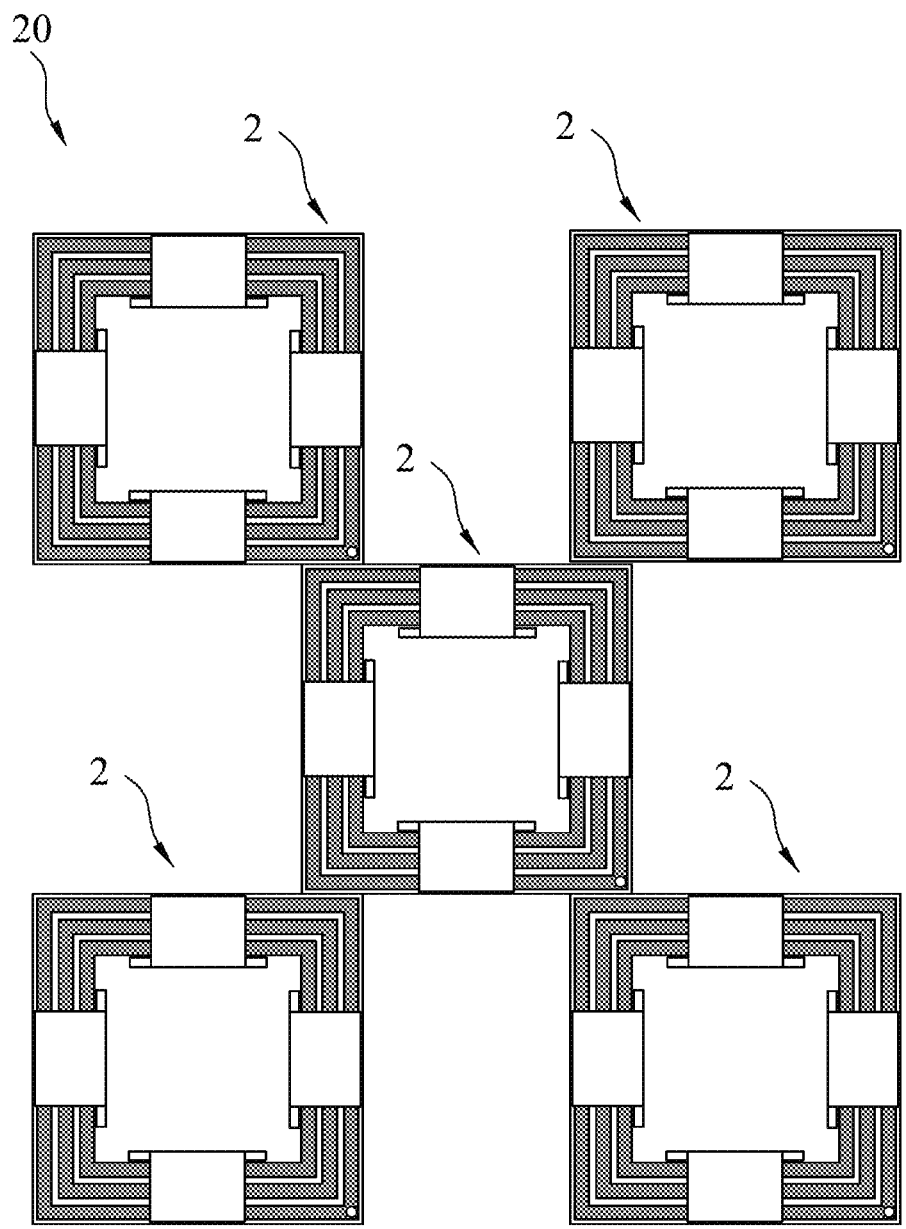
FIG. 8 is a schematic top view of a modification of the inductive device including a plurality of the inductive modules of the embodiment.
Figure 9:
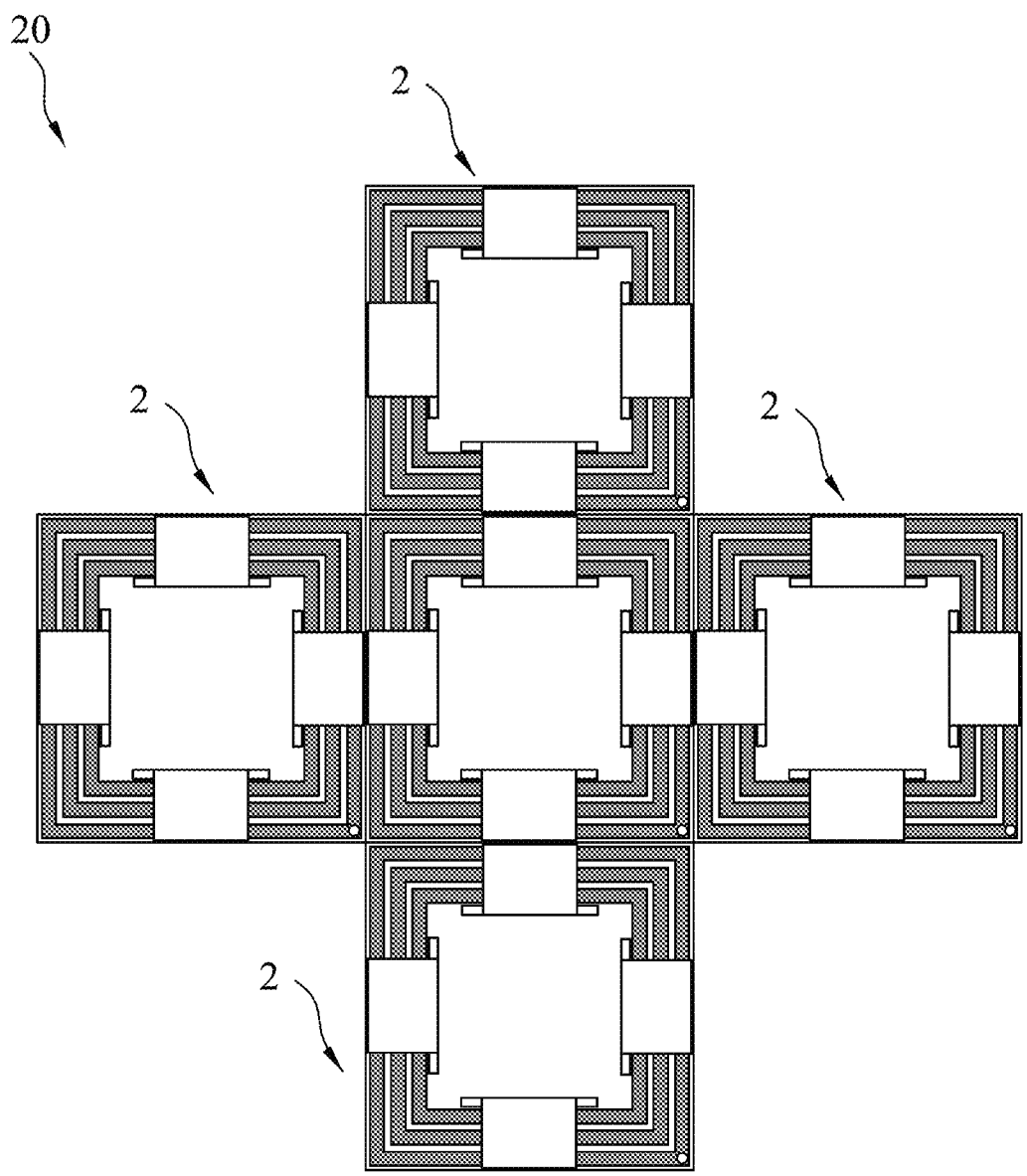
FIG. 9 is a schematic top view of another modification of the inductive device including a plurality of the inductive modules of the embodiment.

Referring to FIG. 8, a modification of the inductive device 20 includes five of the inductive modules 2. In this modification, one of the inductive modules 2 is disposed at a center of the inductive device 20, and the remaining four of the inductive modules 2 are disposed respectively at four corners of the central one of the inductive modules 2 and are spaced apart from one another around the central inductive module 2. As shown in FIG. 9, another modification of the inductive device 20 also includes five of the inductive modules 2. Four of the inductive modules 2 respectively correspond in position to four side edges of one of the inductive modules 2 that is disposed at the center of the inductive device 20. The configuration of the inductive device 20 shown in FIGS. 8 and 9 are merely some examples, and the arrangement of the inductive modules 2 is not limited to these examples.

Figure 10:
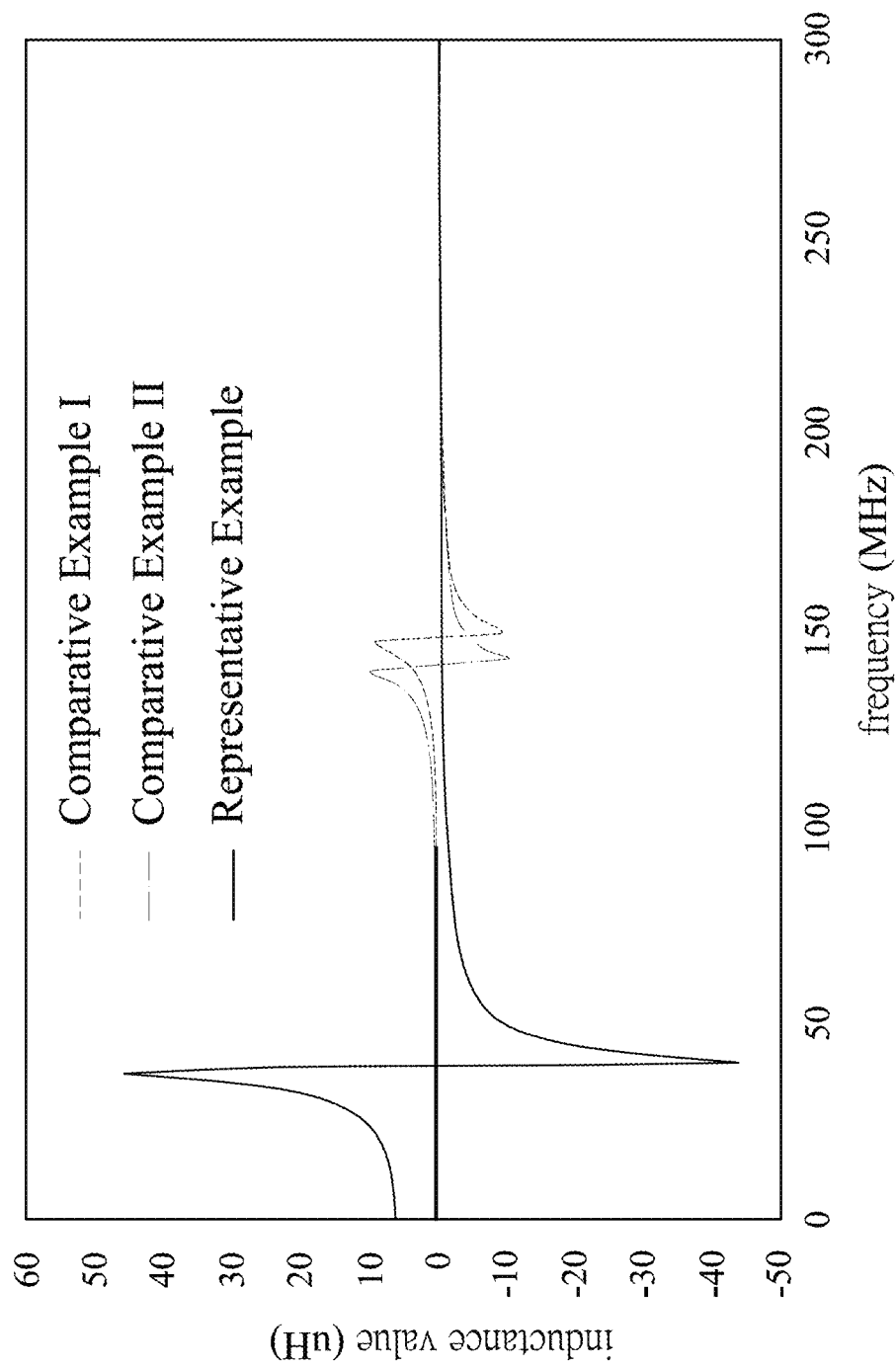
FIG. 10 is a plot diagram illustrating relationships of frequency and inductance value for the inductive module of the disclosure, Comparative example I, and Comparative example II.

Referring to FIG. 10, which is a diagram showing plots of inductance values of a representative example of the disclosure, comparative example I, and comparative example II relative to operating frequencies thereof. Comparative example I is an inductive module that includes a plurality of closed loop coils but not the magnetic units 231 of the embodiment, and the experimental results thereof are depicted by a dashed line. Comparative example II is another inductive module including a magnetic unit disposed at the center of a substrate, and the experimental results thereof are depicted by a dot-dashed line. The representative example of the disclosure is the inductive module 2 shown in FIGS. 2 and 3, and the experimental results thereof are depicted by a solid line. As seen in the experimental results, by virtue of the structure of the magnetic units 231 that are arranged in pairs and each pair of the magnetic units 231 that are located at symmetrical positions to partially cover the closed loop coils 221, an inductance value generated by the representative example of the disclosure is significantly larger than that of Comparative example I and Comparative example II, especially when the operating frequency ranges between 0 Mhz to 50 MHz.

To sum up, by virtue of the design of the inductance module 2 of the present disclosure that includes the magnetic units 231 disposed at symmetrical positions to partially cover the closed loop coils 221 and respectively having the openings 230, the inductance value generated by the closed loop coils 221 can be significantly increased without adopting the conventional approach of increasing the number of coil turns and the length of the closed loop coils 221 because the conventional approach may also increase internal resistance of the closed loop coils 221 and adversely affect transmission efficiency. By pursuing the design of the inductance module 2 of the present disclosure, the inductance module 2 can now be smaller in size and be used in implantable medical devices. In this way, referring back to FIG. 1, in case of the efficiency of wireless charging of the medical devices is reduced due to misalignment or misorientation between the wireless charger 12 and the brain pacemaker 11, e.g., the wireless charger 12 is tilted relative to the brain pacemaker 11, since the inductive module 2 of the present disclosure provides a relatively large inductance value, the transmission efficiency between the wireless charger 12 and the brain pacemaker 11 can still be maintained at a certain level to meet the charging demand.

In the description above, for the purposes of explanation, numerous specific details have been set forth in order to provide a thorough understanding of the embodiments. It will be apparent, however, to one skilled in the art, that one or more other embodiments may be practiced without some of these specific details. It should also be appreciated that reference throughout this specification to "one embodiment," "an embodiment," an embodiment with an indication of an ordinal number and so forth means that a particular feature, structure, or characteristic may be included in the practice of the disclosure. It should be further appreciated that in the description, various features are sometimes grouped together in a single embodiment, figure, or description thereof for the purpose of streamlining the disclosure and aiding in the understanding of various inventive aspects, and that one or more features or specific details from one embodiment may be practiced together with one or more features or specific details from another embodiment, where appropriate, in the practice of the disclosure.

While the disclosure has been described in connection with what is considered the exemplary embodiment, it is understood that this disclosure is not limited to the disclosed embodiment but is intended to cover various arrangements included within the spirit and scope of the broadest interpretation so as to encompass all such modifications and equivalent arrangements.

What is claimed is:

1. An inductive module with a miniaturized metamaterial structure, comprising:
   an insulating substrate that has a first surface and a second surface opposite
   to said first surface, and a through hole extending between said first surface and said second surface;
   two coil units, which are respectively disposed on said first surface and said second surface of said insulating substrate, and electrically connected to each other through said through hole, each of said coil units including at least one closed loop coil; and
   at least one magnetic unit that corresponds in position to a portion at least one of said coil units, that surrounds said portion of said at least one of said coil units, and that has an opening.

2. The inductive module of claim 1, wherein said at least one magnetic unit corresponds in position to a portion of each of said coil units and surrounds said portion of each of said coil units by extending from one of said coil units to the other one of said coil units.

3. The inductive module of claim 2, wherein said at least one magnetic unit includes a plurality of magnetic units which are spaced apart from one another and each of which has said opening.

4. The inductive module of claim 3, wherein the quantity of said magnetic units is of an even number, and said magnetic units are located at symmetrical positions to cover said coil units.

5. The inductive module of claim 4, wherein said magnetic units are arranged in pairs, and said openings of each pair of said magnetic units face towards or away from each other.

6. The inductive module of claim 4, wherein each of said magnetic units is C-shaped.

7. The inductive module of claim 4, wherein each of said magnetic units is E-shaped, and has an intermediate projection (232) inserted in said insulating substrate and pointing towards said opening.

8. The inductive module of claim 1, wherein each of said coil units includes a plurality of closed loop coils, and said closed loop coils are formed concentrically and proximally to an outer peripheral edge of said insulating substrate.

9. The inductive module of claim 1, wherein said insulating substrate is a printed circuit board.

10. The inductive module of claim 1, wherein said coil units are made of copper.

11. The inductive module of claim 1, wherein said magnetic unit is made of a soft magnetic material.

12. The inductive module of claim 1, wherein said at least one magnetic unit includes a plurality of magnetic units, each of which has said opening and which are angularly spaced apart from one another around a center of said at least one closed loop coil, said magnetic units being arranged in pairs, each pair of said magnetic units being located respectively at two positions that are symmetrical with respect to said center, and each of said magnetic units forming an open loop and partially loops around said portion of said at least one closed loop coil.

13. The inductive module of claim 12, wherein each of said magnetic units has two free ends disposed at two opposing sides of said openings, and an insert portion that is inserted in said insulating substrate and that faces said opening.

14. The inductive module of claim 13, wherein each of said magnetic units is C-shaped.

15. The inductive module of claim 13, wherein each of said magnetic units is E-shaped, said insert portion having an intermediate projection pointing towards said opening.

16. An inductive device, comprising:
   a plurality of inductive modules each including an insulating substrate that has
      a first surface and a second surface opposite to said first surface, and
      a through hole extending between said first surface and said second surface;
   two coil units, which are respectively disposed on said first surface and said second surface of said insulating substrate, and electrically connected to each other through said through hole, each of said coil units including at least one closed loop coil; and
   at least one magnetic unit that corresponds in position to a portion of at least one of said coil units and that surrounds said portion of said at least one of said coil units, wherein said inductive modules are arranged in an array and juxtaposed with one another.

* * * * *